US00PP21401P2

(12) United States Plant Patent
Glenn

(10) Patent No.: US PP21,401 P2
(45) Date of Patent: Oct. 19, 2010

(54) ***EUPHORBIA* PLANT NAMED 'ASCOT RAINBOW'**

(50) Latin Name: *Euphorbia×martinii*
Varietal Denomination: Ascot Rainbow

(76) Inventor: David Glenn, Burnside Lesters Rd, Ascot (AU) 3364

( * ) Notice: Subject to any disclaimer, the term of this patent is extended or adjusted under 35 U.S.C. 154(b) by 0 days.

(21) Appl. No.: 12/460,692

(22) Filed: Jul. 22, 2009

(51) Int. Cl.
*A01H 5/00* (2006.01)

(52) U.S. Cl. ..... Plt./302

(58) Field of Classification Search ..... Plt./302
See application file for complete search history.

*Primary Examiner*—Kent L Bell

(57) ABSTRACT

A new cultivar of *Euphorbia* plant named 'ASCOT RAINBOW' that is distinguishable by compact slightly spreading habit, red stems, and variegated cream-yellow and gray-green foliage that turns red-pink with the onset of winter. In combination these traits set 'ASCOT RAINBOW' apart from all other existing varieties of *Euphorbia* known to the inventor.

3 Drawing Sheets

Genus: *Euphorbia*.
Species: ×*martinii*.
Denomination: 'ASCOT RAINBOW'.

BACKGROUND OF THE INVENTION

The present invention relates to a new and distinct cultivar of spurge, suitable for use in bed, border, container, or as a specimen plant in the landscape. The new invention, in the Euphorbiaceae family, is known botanically as *Euphorbia*× *martinii*, and will be referred to hereinafter by the cultivar name 'ASCOT RAINBOW'.

The new *Euphorbia* cultivar named 'ASCOT RAINBOW' was discovered by the breeder in Victoria, Australia as a naturally occurring branch sport of the parent plant, namely an individual plant of *Euphorbia*×*martinii* (species, unpatented). The inventor selected 'ASCOT RAINBOW' in 2005 based on the criteria of variegated cream-yellow and gray-green foliage that turns red-pink with the onset of winter.

The parent of 'ASCOT RAINBOW' is an individual *Euphorbia*×*martinii*. 'ASCOT RAINBOW' is distinguishable from the parent by variegated foliage. The closest comparison plant known to the inventor is *Euphorbia* 'Inneuphhel' (U.S. Plant Pat. No. 17,555) which exhibits a short mounding habit and bears cream-white variegation covering a small area of the leaf margin. 'ASCOT RAINBOW' is distinguishable from the comparison plant by height ('ASCOT RAINBOW' is approximately twice as tall after one growing season) and variegated cream-yellow and gray-green leaves (the cream-yellow color of 'ASCOT RAINBOW' covers a larger area of the leaf margin).

'ASCOT RAINBOW' exhibits compact slightly spreading habit, sturdy red stems, markedly variegated flowers that bloom spring through summer, and variegated foliage. The flowers are tubular in shape and cream-yellow, lime, green, and red in color. Foliage exhibits tones of cream-yellow, gray-green, and red-pink color with the onset of winter. The red-pink color will result also from drought stress, however too much fertilizer, particularly increased levels of nitrogen in the soil will inhibit the development of red-pink foliage color. 'ASCOT RAINBOW' is extremely tolerant of heat and dry conditions. Cultural requirements include full sun, porous well-draining soil, and minimal to moderate water. 'ASCOT RAINBOW' grows to 50 cm. in height and 40 cm. in width during the first growing season, and reaches 90 cm. in height and 80 cm. in width at maturity. 'ASCOT RAINBOW' is classified as hardy at least in USDA Hardiness Zone 6.

The first asexual reproduction of 'ASCOT RAINBOW' was accomplished in 2005. Asexual propagation was carried out by the inventor, in Victoria, Australia and the method used was stem cuttings. Since that time under careful observation 'ASCOT RAINBOW' has been determined fixed, stable, and reproduces true to type in successive generations of asexual propagation.

SUMMARY OF THE INVENTION

The following traits have been repeatedly observed and represent the distinguishing characteristics of the new *Euphorbia* cultivar named 'ASCOT RAINBOW'. These traits in combination distinguish 'ASCOT RAINBOW' from all other existing varieties of *Euphorbia* known to the inventor. 'ASCOT RAINBOW' has not been tested under all possible conditions and phenotypic differences may be observed with variations in environmental, climatic, and cultural conditions, however, without any variance in genotype.

1. 'ASCOT RAINBOW' exhibits compact slightly spreading habit.
2. 'ASCOT RAINBOW' exhibits variegated cream-yellow and gray-green foliage that turns red-pink with the onset of winter.
3. 'ASCOT RAINBOW' exhibits tubular flowers that are variegated cream-yellow, lime, green, and red in color.
4. 'ASCOT RAINBOW' is extremely tolerant of heat and dry conditions.
5. 'ASCOT RAINBOW' reaches 90 cm. in height and 80 cm. in width at maturity.
6. 'ASCOT RAINBOW' is asexually propagated using the method of stem cuttings.
7. 'ASCOT RAINBOW' is hardy at least to USDA Hardiness Zone 6.

BRIEF DESCRIPTION OF THE DRAWINGS

The accompanying color drawings illustrate the overall appearance of the new *Euphorbia* cultivar named 'ASCOT RAINBOW' showing color as true as it is reasonably possible to obtain in color reproductions of this type. Color in the drawings may differ from color values cited in the detailed botanical description, which accurately describe the actual colors of 'ASCOT RAINBOW'.

The drawing labeled

The drawing labeled

The drawing labeled

Figure 1:
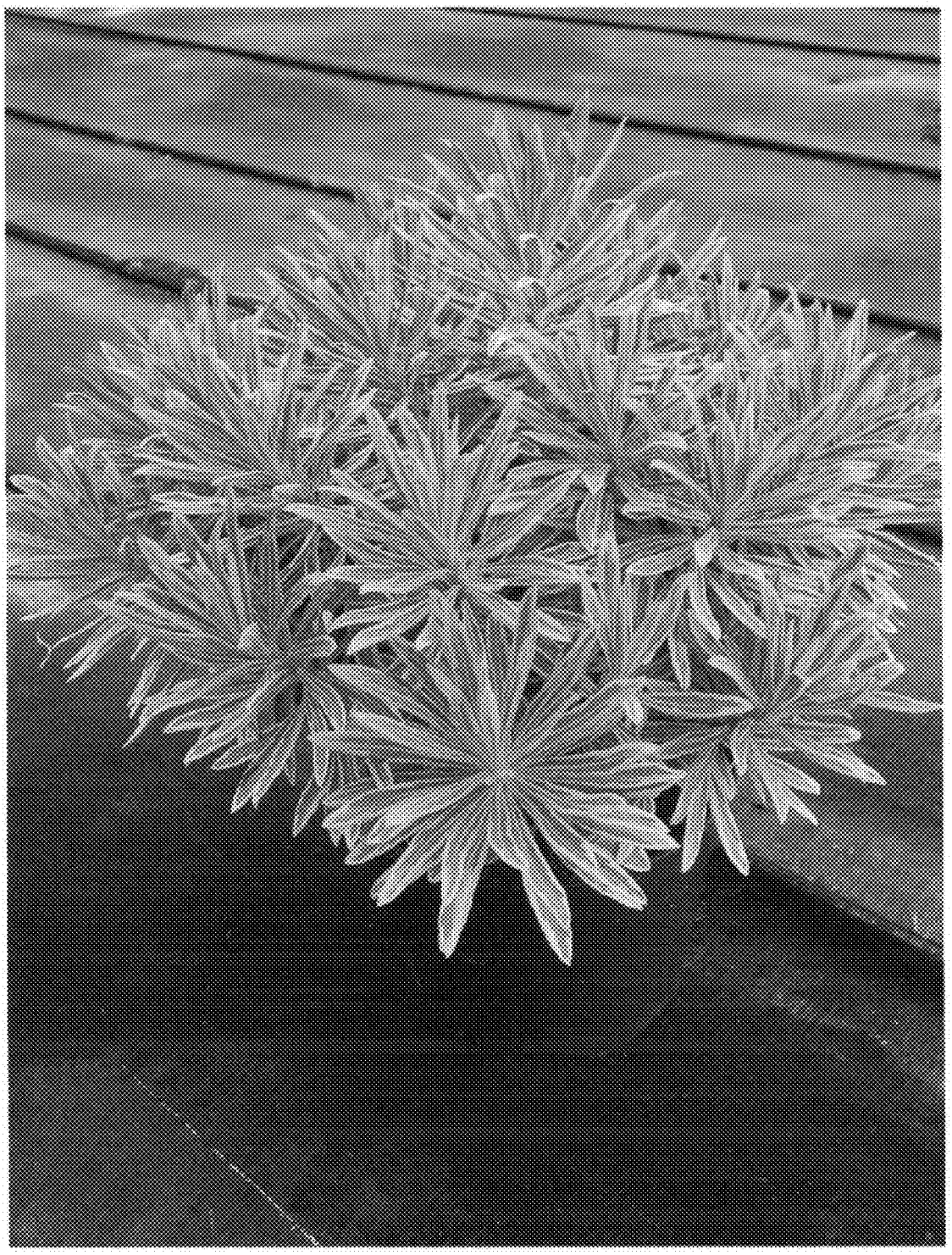
FIG. 1 depicts a whole plant in spring.
Figure 2:
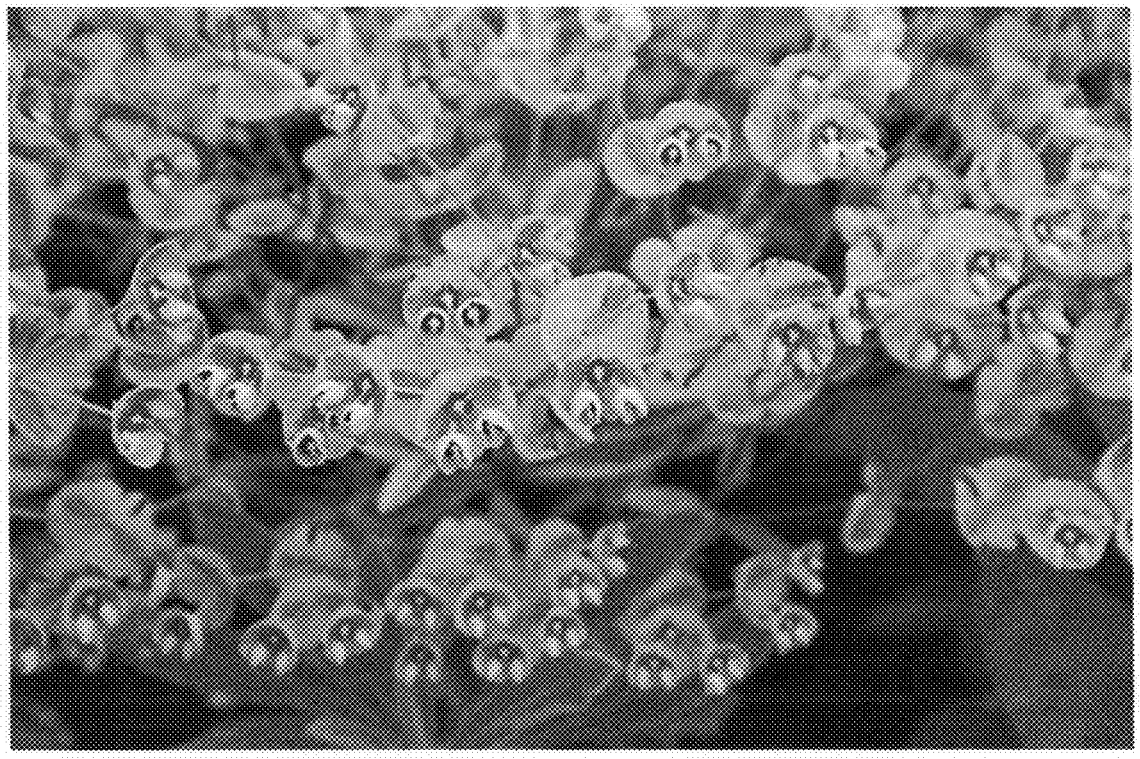
FIG. 2 depicts a close-up view of the flower in summer.
Figure 3:
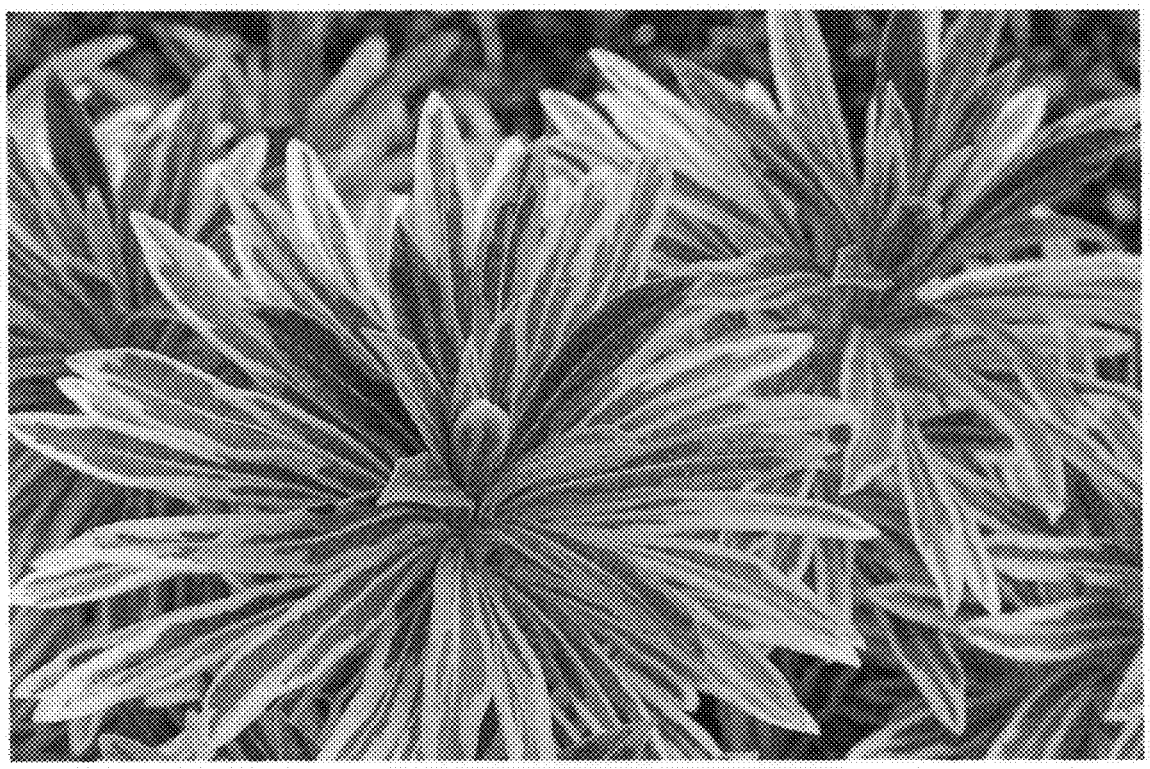
FIG. 3 depicts the red-pink color of the foliage in fall.

All drawings were made in Melbourne, Australia using conventional techniques and although flower and foliage color may appear different from actual color due to light reflectance, they are as accurate as possible by conventional photography.

BOTANICAL DESCRIPTION OF THE PLANT

The following is a detailed botanical description of the new *Euphorbia* cultivar named 'ASCOT RAINBOW'. Observations, measurements, values and comparisons were collected in Arroyo Grande, Calif. from 12-month-old 2-litre container plants grown out-of-doors. Color determinations are made in accordance with the 2001 edition of The Royal Horticultural Society Colour Chart of London, England, except where general color terms of ordinary dictionary significance are used. The growing requirements of the new variety are similar to the species.

Botanical classification: *Euphorbia×martinii* 'ASCOT RAINBOW'.

Family: Euphorbiaceae.

Genus: *Euphorbia.*

Species: *×martinii.*

Denomination: 'ASCOT RAINBOW'.

Common name: Spurge.

Commercial classification: Sub-shrub.

Parentage: *Euphorbia×martinii* 'ASCOT RAINBOW' was discovered as a naturally occurring branch sport of the parent an individual *Euphorbia martinii.*

Asexual propagation method: Stem cuttings.

Rooting habit: Fine and fibrous.

Time to develop roots: 9-12 weeks are needed for roots to develop on an initial cutting.

Temperature recommended to develop roots: 18° Centigrade.

Crop time: 8-9 months are needed to produce a finished 1-liter container from a rooted cutting.

Habit: Compact slightly spreading habit.

Use: Bed, border, container, or specimen plant for the landscape.

Type: Perennial.

Vigor: Vigorous.

Plant dimensions (first season): 50 cm. in height and 40 cm. in width.

Plant dimensions (at maturity): 90 cm. in height and 80 cm. in width.

Cultural requirements: Full sun, porous well-draining soil, and minimal to moderate water.

Pest or disease susceptibility: Susceptible to two-spotted mite.

Disease and pest resistance: None known to the inventor.

Hardiness: Classified at least as hardy as USDA Hardiness Zone 6.

Seasonal traits: Blooms spring through summer.

Special considerations: Extremely tolerant to heat and dry conditions. Increased amounts of fertilizer particularly nitrogen inhibits foliage from turning red-pink in color.

Hazardous considerations: All parts exude a white milky substance or sap when bruised. The sap of 'ASCOT RAINBOW' is toxic and will elicit dermal irritation.

Stem:

- *Branching habit.*—Divergent.
- *Quantity* (*average*).—25 per 1.5 liter container plant.
- *Dimensions* (*average*).—15 cm. in length and 0.60 cm. in width.
- *Shape.*—Columnar.
- *Surface* (*range*).—Pubescent to villous.
- *Color.*—182A.
- *Scar dimensions.*—1 mm. in height and 3 mm. in width.
- *Scar color.*—156A.
- *Scar shape.*—Spindle-shaped.
- *Internode length* (*range*).—1 cm. to 2 cm.

Foliage:

- *Type.*—Evergreen.
- *Arrangement.*—Whorled.
- *Division.*—Simple.
- *Shape.*—Oblanceolate.
- *Length* (*range*).—6.50 cm. to 8.50 cm.
- *Width* (*range*).—0.90 cm. to 1.50 cm.
- *Leaf apex.*—Acute.
- *Leaf base.*—Attenuate.
- *Quantity* (*range*).—50-70 leaves per stem.
- *Venation pattern* (*adaxial and abaxial surfaces*).—Pinnate with visible mid-vein.
- *Mid-vein color* (*adaxial surface*).—161A.
- *Mid-vein color* (*abaxial surface*).—147D.
- *Margin.*—Entire.
- *Adaxial surface* (*range*).—Pubescent to villous.
- *Abaxial surface* (*range*).—Pubescent to villous.
- *Attachment.*—Sessile.
- *Leaf color* (*adaxial surface*).—146B and 161A.
- *Leaf color* (*abaxial surface*).—147C and 161A.
- *Leaf color with onset of winter* (*adaxial surface*).—146B, 161A and 182A all individually present.
- *Leaf color with the onset of winter* (*abaxial surface*).—147C, 161A and 182A all individually present.
- *Leaf fragrance.*—Pungent scent.

Inflorescence:

- *Blooming seasons.*—Spring through summer.
- *Type.*—Cyathium.
- *Shape.*—Tubular.
- *Cyathium quantity* (*average per stem*).—More than 100.
- *Cyathium quantity* (*average per rachis*).—2.
- *Cyathium dimensions.*—1 cm. in diameter and 0.50 cm. in depth.
- *Cyathium color.*—161D, 146A, 154A and 185A all individually present.
- *Aspect.*—Facing upward and outward.
- *Rachis color.*—183A.
- *Rachis dimensions* (*average*).—4.5 cm. in length and 2 mm. in diameter.
- *Rachis shape.*—Cylindrical.
- *Rachis surface.*—Pubescent.
- *Internode* (*range*).—0.75 cm. to 2 cm.
- *Bract quantity* (*range*).—12-14 per rachis.
- *Bract fused or unfused.*—Basally fused.
- *Bract color* (*adaxial surface*).—146A, 154A and 161D all individually present.
- *Bract color* (*abaxial surface*).—146A, 154A and 161D all individually present.
- *Bract margin.*—Entire.
- *Bract shape.*—Reniform.

*Bract apex* (*range*).—Obtuse to rounded.
*Bract base.*—Truncate.
*Bract height* (*range*).—0.50 cm. to 1 cm.
*Bract width* (*range*).—0.50 cm. to 1.50 cm.
*Bract surfaces* (*adaxial and abaxial*).—Puberulent.
*True perianth.*—Absent.
*Involucre shape.*—Tubular.
*Involucre dimensions.*—4 mm. in diameter and 5 mm. in length.
*Involucre surface.*—Puberulent.
*Involucre color.*—161D.
*Involucre apex.*—Rounded.
*Staminate flower.*—Apetalous. Staminate flower quantity (average): 4 per cyathium. Stamens: 1 per staminate flower. Stamen color: 146D. Stamen length: 2 mm. Stamen surface: Lanate. Nectary gland: 4 per cyathium. Nectary gland width: <1.50 mm. Nectary gland surface: Smooth. Nectary gland color: 185A.
*Pistillate flower.*—Apetalous. Pistillate flower quantity: 1 per cyathium. Pistil: 1 in number. Pistil length: 8 mm. Pistil color: 146D. Style: 3 in number joined at base. Style length: 2 mm. Style color: 146D. Stigma: 3 in number. Stigma color: 146D. Stigma shape: Bifid. Stigma width: <0.50 mm. Ovary shape: Globose. Ovary dimensions: 1.50 mm. in height and 1.50 mm. in diameter. Ovary surface: Lanate. Ovary color: 146D. Ovary position: Superior.
*Lastingness of individual cyathium* (*range*).—20-35 days.
*Cyathium fragrance.*—Pungent scent.
Seed: No seed has been observed to date.

The invention claimed is:

1. A new and distinct cultivar of *Euphorbia* plant named 'ASCOT RAINBOW' as described and illustrated herein.

* * * * *